(12) United States Patent
Shinn, II et al.

(10) Patent No.: US 7,234,362 B2
(45) Date of Patent: Jun. 26, 2007

(54) SUBSURFACE MATERIAL PROPERTY MEASUREMENT

(75) Inventors: James D. Shinn, II, South Royalton, VT (US); Charles R. Reed, Jr., Tomball, TX (US); Stephen P. Farrington, Stockbridge, VT (US); Kenneth A. McIntosh, Bethel, VT (US)

(73) Assignee: Applied Research Associates, Inc., Albuquerque, NM (US)

( * ) Notice: Subject to any disclaimer, the term of this patent is extended or adjusted under 35 U.S.C. 154(b) by 124 days.

(21) Appl. No.: 10/995,024

(22) Filed: Nov. 22, 2004

(65) Prior Publication Data

US 2006/0107772 A1   May 25, 2006

(51) Int. Cl.
*G01N 3/00*   (2006.01)

(52) U.S. Cl. ....................................................... 73/784
(58) Field of Classification Search ............... 73/9, 73/784, 73, 864.74; 175/40, 50, 58; 250/253–255
See application file for complete search history.

(56) References Cited

U.S. PATENT DOCUMENTS

| | | | |
|---|---|---|---|
| 2,701,121 A | 2/1955 | Bull | |
| 3,163,241 A | 12/1964 | Daigle et al. | |
| 3,481,188 A | 12/1969 | Mori | |
| 3,500,678 A | 3/1970 | Van Romondt Vis | |
| 3,875,796 A | 4/1975 | Gilliard | |
| 3,906,781 A * | 9/1975 | Vlasblom | ...................... 73/84 |
| 3,916,684 A | 11/1975 | Rundell | |
| 4,085,509 A | 4/1978 | Bell et al. | |
| 4,400,970 A | 8/1983 | Ali | |
| 4,405,231 A * | 9/1983 | Shemyakin et al. | .......... 356/34 |
| 4,499,955 A | 2/1985 | Campbell et al. | |
| 4,499,956 A | 2/1985 | Campbell et al. | |
| 4,530,236 A | 7/1985 | van den Berg | |
| 4,554,819 A | 11/1985 | Ali | |
| 4,601,354 A | 7/1986 | Campbell et al. | |
| 4,638,872 A | 1/1987 | Park et al. | |
| 4,770,030 A | 9/1988 | Smith | |
| 5,125,266 A | 6/1992 | Ingram et al. | |
| 5,127,261 A | 7/1992 | Ingram et al. | |
| 5,150,622 A | 9/1992 | Vollweiler | |
| 5,168,765 A * | 12/1992 | Broussard | ................ 73/864.74 |
| 5,186,263 A * | 2/1993 | Kejr et al. | ..................... 175/20 |
| 5,339,679 A | 8/1994 | Ingram et al. | |
| 5,425,428 A | 6/1995 | Chatagnier et al. | |
| 5,474,140 A | 12/1995 | Stevens | |
| 5,487,431 A | 1/1996 | Webb | |
| 5,578,769 A * | 11/1996 | Warrington et al. | ..... 73/864.74 |
| 5,587,540 A | 12/1996 | Meyer | |

(Continued)

FOREIGN PATENT DOCUMENTS

GB    1 433 265    4/1976

*Primary Examiner*—Robert Raevis
(74) *Attorney, Agent, or Firm*—Fish & Richardson P.C.

(57) ABSTRACT

Subsurface material property measurements, such as soil or chemical properties, are obtained in situ by a direct push method that includes rotating a ring bit at the end of a casing to drill through subsurface materials, lowering a measurement probe through the advanced casing, extending the lowered measurement probe through the ring bit, and advancing the extended probe through the soil at a controlled rate while gathering material property data from sensors attached to the probe. The probe may be withdrawn for drilling, and then replaced for further data gathering.

58 Claims, 8 Drawing Sheets

U.S. PATENT DOCUMENTS

| | | |
|---|---|---|
| 5,591,902 A | 1/1997 | Castagner |
| 5,616,833 A | 4/1997 | Andersson |
| 5,744,730 A | 4/1998 | Ballard et al. |
| 5,886,253 A | 3/1999 | Joustra |
| 5,902,939 A * | 5/1999 | Ballard et al. ........... 73/863.12 |
| 5,979,569 A | 11/1999 | Heller |
| 6,062,090 A * | 5/2000 | Bachhuber et al. ........... 73/784 |
| 6,230,820 B1 | 5/2001 | Cordry |
| 6,431,006 B1 * | 8/2002 | Henke et al. .................. 73/784 |
| 6,594,881 B2 * | 7/2003 | Tibbitts ....................... 29/450 |
| 6,644,423 B2 * | 11/2003 | Bratton et al. ................ 175/58 |

\* cited by examiner

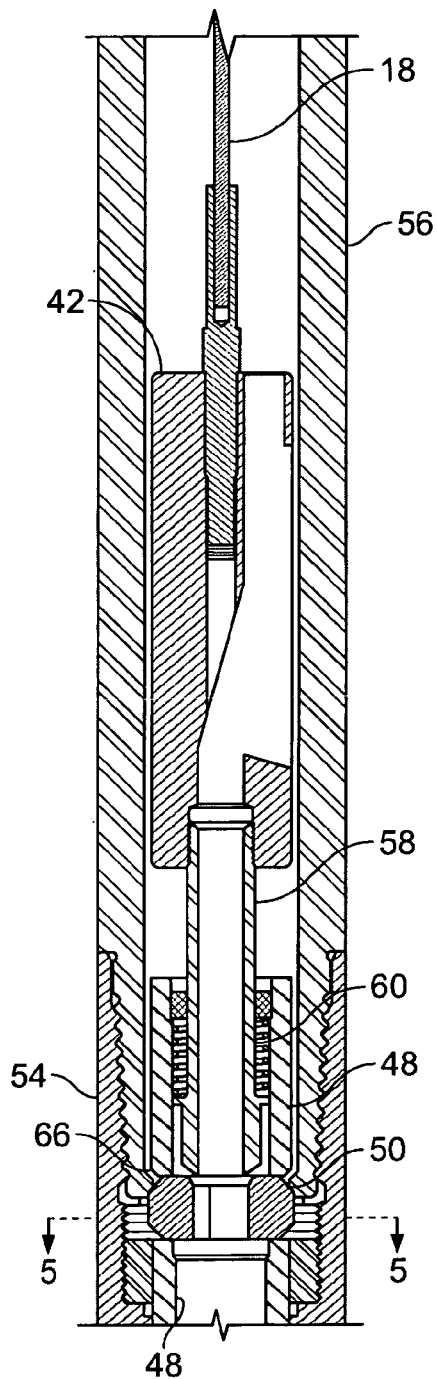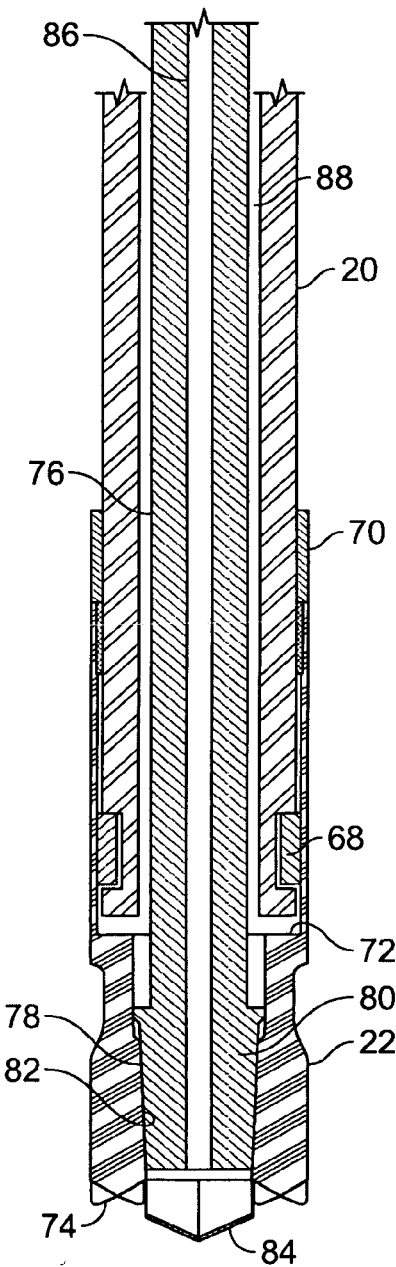
FIG. 4                                     FIG. 6

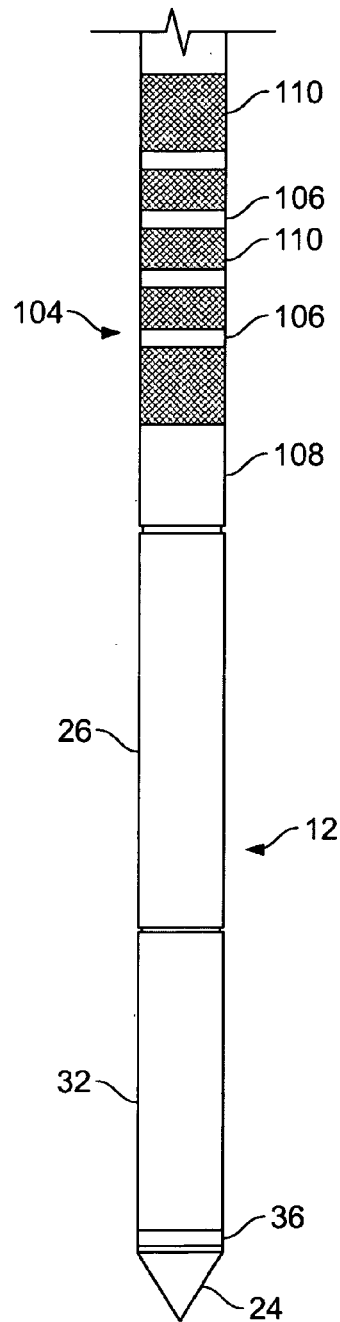
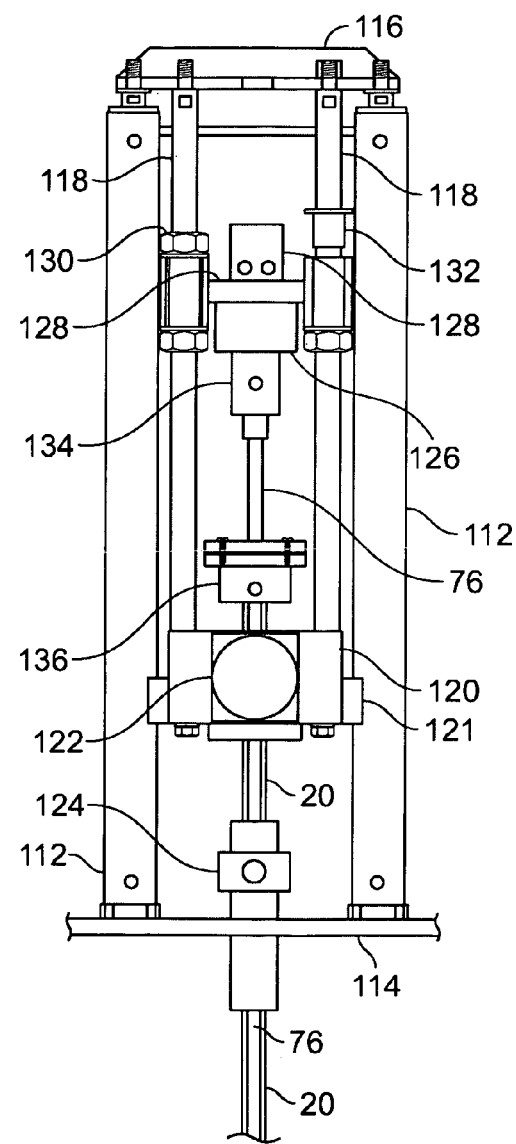
FIG. 10                    FIG. 11

SUBSURFACE MATERIAL PROPERTY MEASUREMENT

TECHNICAL FIELD

This invention relates to methods of obtaining subsurface material property measurements in soil, and to tools for such methods.

BACKGROUND

Sometimes the properties of subsurface materials, such as soil, liquids, gasses or chemicals, are determined by bringing samples of the material to the surface for inspection and measurement. Sometimes it is preferred to obtain such information in situ, that is, underground where the material is found. Information can be gathered from sensors, for example, as the sensors are pushed through the soil, to obtain a log or chart of information as a function of depth or position.

Cone Penetrometer Testing (CPT) is one known method of obtaining logs of subsurface material properties. In general terms, CPT features a cone-tipped probe pushed in a non-rotary sense through the soil, typically in a vertical direction. Sensors in the probe measure such properties as bearing load and soil friction, from which various other properties of the soil can be inferred. Other sensors are also included in the probe, such as for measuring subsurface pore fluid pressure. Various other sensors have also been developed for deployment by CPT methods. In environmentally sensitive sites, direct push techniques like CPT are preferred because the relatively small holes they leave in soil can be filled with grout as the probes are withdrawn, and do not generate the volume of tailings produced by drill-sampling methods.

The probe depths obtainable by direct push methods like CPT are limited, primarily due to limits on the amount of push force that can be applied. While depths of 100 meters or more have been obtained in some geologies, depths of only about 50 meters are more common, as soil friction on the outer surface of the probe and push rods eventually exceeds the amount of downward force that can be safely applied at the surface. In other cases, an immovable obstruction, such as bedrock, is encountered. Either event is called "refusal" and represents the extent of the depth obtainable for that push.

SUMMARY

We have realized that some of the limitations of direct push methods can be overcome by incorporating a rotatable bit at the lower end of the push rods, or on a rotatable casing about the push rods.

According to one aspect of the invention, a method of obtaining subsurface material property measurements in situ is provided. The method includes pushing a first measurement probe through soil at a controlled rate to a first depth while gathering material property data from sensors attached to the probe, with the probe extending beyond a distal end of a casing pushed through the soil with the probe and having an outer surface that slides linearly against the soil as the probe and casing are pushed through the soil. While leaving the casing in the soil, the first probe is withdrawn from the distal end of the casing, and then the distal end of the casing is rotated to displace subsurface materials to advance the casing with the first probe withdrawn.

In many particularly useful examples, the method includes, after advancing the casing, lowering a second measurement probe to extend through the distal end of the casing, and then pushing the second measurement probe through the soil at a controlled rate to a second depth while gathering additional material property data from sensors attached to the second probe.

In some cases the second probe is the first probe, redeployed through the distal end of the casing.

In some embodiments, the second probe is lowered to the distal end of the casing on a wire line, and force to push the second probe through the soil is applied through the casing. In some instances, the casing is advanced by pushing as the second probe is pushed through the soil. In many cases the first probe is withdrawn from the distal end of the casing on a wire line, and force to push the first probe through the soil is applied through the casing.

In some configurations, the second probe (and/or the first probe) includes a sensor responsive to load bearing against a distal end of the second probe in a push direction, and/or a sensor responsive to soil friction load against an exposed surface of the second probe as the second probe is pushed through the soil.

The second and/or first probe may also include a sensor responsive to resistivity, soil moisture, fluorescence, pore water pressure or light, and/or be configured to collect a sample of subsurface material.

In some instances, the method also includes combining data gathered with the first probe with data gathered from the second probe to create a subsurface property data log extending to the second depth. The data log may include a data-less region corresponding to soil through which the casing was advanced by rotating, or include data obtained while rotating the distal end of the casing with the first probe withdrawn.

After advancing the casing by rotating, the casing may be pulled back to form clearance beyond the distal end of the casing to accommodate the second probe during lowering.

In the presently preferred embodiment, withdrawing the first probe removes the first probe from the casing and exposes an opening through the distal end of the casing. The method may also include, prior to rotating the distal end of the casing, lowering a center bit into the opening, wherein rotating the distal end of the casing includes rotating the center bit. In some cases, the center bit is lowered on a drive rod extending up along the casing, the center bit being rotated by rotating the drive rod. In some cases, the distal end of the casing includes a rotatable ring bit engaged by the lowered center bit, such that rotating the center bit rotates the ring bit.

The casing may be advanced, after the first probe is withdrawn, by air rotary or rotary wash drilling, for example.

For some applications, the method also includes, after withdrawing the first probe, lowering a sampling module to the distal end of the casing and collecting a sample of subsurface material with the sampling module. The subsurface material may include soil, liquid and/or gas. The sample may be collected by advancing the casing after lowering the sampling module, for example.

Preferably, the first probe extends at least three times an outer diameter of the first probe beyond the distal end of the casing, for obtaining material property measurements in soil undisturbed by advance of the casing.

For most applications, it is preferred that the first probe and the casing are pushed through the soil in a non-rotary sense, preferably at a constant rate of about two centimeters per second. By 'constant rate' we mean to exclude occasional interruptions in the advance of the probe, such as to add additional lengths of push rod.

The method also includes, in many cases, predetermining a push load at which the pushing of the first probe through the soil will be terminated and the first probe withdrawn.

In some examples, the method includes, prior to rotating the distal end of the casing, lowering a percussion hammer to engage the distal end of the casing, and, while rotating the distal end of the casing, activating the percussion hammer to advance the casing through the soil. The percussion hammer may be activated pneumatically, for example.

For some applications, such as environmentally sensitive sites, the method also includes withdrawing the casing from the soil while filling an exposed hole beneath the withdrawn casing with grout supplied through the casing. The grout may be delivered through a tube extending from above ground to a grout outlet module lowered into the casing after the first probe is withdrawn, for example.

In some cases, rotating the distal end of the casing advances the casing into bedrock. The method may also include setting an anchor into the bedrock.

To provide additional near-surface support for the casing, for example, in some instances the method includes lowering a casing support tube into the soil, the support tube extending above the soil and defining an annular passage through which the casing is advanced. Preferably, the support tube extends into the soil to a depth of at least two meters.

In many configurations, the distal end of the casing includes a rotatable ring bit, while a major extent of the casing is pushed in a non-rotary sense as the ring bit is rotated.

In some instances the method includes, while rotating the distal end of the casing, monitoring drilling parameters to determine relative soil properties.

Another aspect of the invention features another method of obtaining subsurface material property measurements in situ. In this aspect, the method includes rotating a distal end of a hollow casing to displace subsurface materials to advance the casing through soil; lowering a measurement probe through the advanced casing; extending the lowered measurement probe through the distal end of the casing to engage soil below the casing; and advancing the extended probe through the soil at a controlled rate to a first depth while gathering material property data from sensors attached to the probe. The probe has an outer surface that slides linearly against the soil as the probe and casing are advanced through the soil.

In some embodiments, the distal end of the casing is rotated by torque applied by a drive rod extending down through the casing to engage the distal end of the casing. Preferably, the drive rod includes a center bit that rotates with the distal end of the casing to displace subsurface materials. In many cases, the drive rod is removed from the housing prior to lowering the measurement probe. In a preferred configuration, the distal end of the casing includes a ring bit rotated with respect to the casing by the drive rod.

The probe may have any one or more of the features discussed above with respect to the first and second probes. Similarly, this aspect of the invention may include one or more method features discussed above with respect to the first-described aspect of the invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a cross-sectional view of the probe-casing locking mechanism, in an unlocked state.

FIG. 6 is a cross-sectional view of the casing end with a center bit and drive rod deployed.

FIG. 10 is a side view of a soil resistivity probe.

FIG. 11 is a side view of a system for pushing probes and casings and rotating casings.

Like reference symbols in the various drawings indicate like elements.

DETAILED DESCRIPTION

Figure 1:
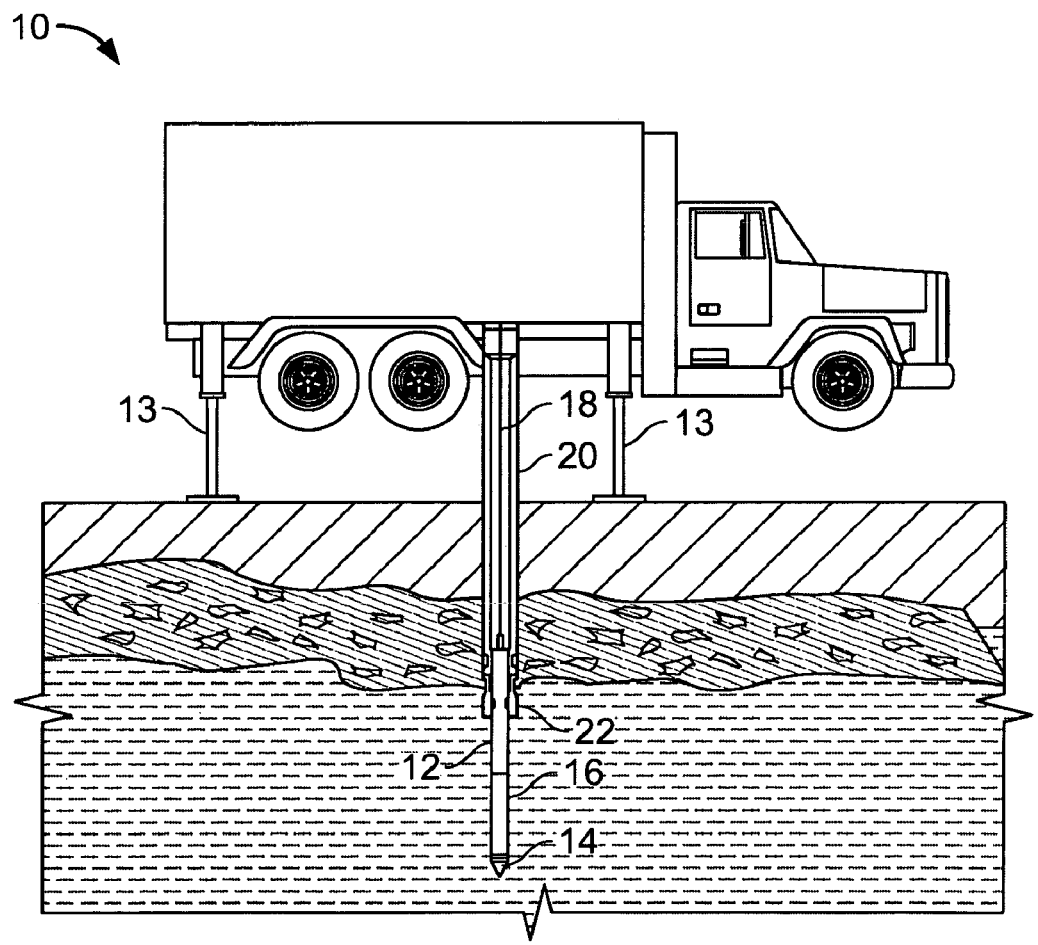
FIG. 1 is an illustration of a direct push truck pushing a probe into soil through a casing.

Referring first to FIG. 1, a test vehicle 10 adapted to collect in-field subsurface data. Vehicle 10 includes a push system for pushing cone penetrometer (CPT) probes 12 or other invasive sensors into the soil along a selected path, either vertical or angled. In many cases the vehicle is first lifted and leveled by hydraulic jacks 13. The pushed probes contain sensors, known in the art and discussed further below, that are responsive to various soil properties. A typical CPT probe configured for geotechnical surveys may contain a tip force load cell 14 and a sleeve friction load cell 16, for example, along with a pore pressure sensor. In many cases, signals from such sensors are relayed electrically or wirelessly up to the push vehicle 10 for logging and analysis. Penetrometer sensors can be used to measure or derive soil compaction, grain size, organic matter content, moisture, temperature and resistivity, as well as other chemical and physical properties. A data acquisition system on-board vehicle 10 collects data from down-hole sensors, and correlates such collected data with depth as determined from a depth gage attached to the push system.

Geotechnical CPT probes are designed to collect stress data as they are pushed, in a non-rotary, quasi-static sense, through virgin soil. Known in the industry as a type of 'direct push' system, CPT systems use hydraulics to apply loads of up to 20–30 tons to push probes of 35 to 65 millimeters in diameter, at steady, interrupted rates of about 2.0 centimeters per second, through sand, clay and other soil types, with the push rate interrupted at fixed intervals to add rod segments to the rod string. Other non-rotary systems that do not produce tailings employ percussion or impact drives to drive samplers or other devices into soil. The depth achievable during steady-push data logging, such as by CPT, is limited by the static load that can be applied at the top of the push rod string, and that can be withstood by the rods and probes.

Many CPT push vehicles are adapted to push a probe rigidly attached at the end of a string of hollow push rods, and to retrieve the probe by pulling up the entire string of push rods. The CPT system shown in FIG. 1 is a form of 'wireline' system, in that the probe 12 is retrievable through the hollow rod string, without removing the rod string from the ground, on a flexible cable 18. As will be discussed below, various probes and samplers can be retrieved and deployed through the submerged rod string on cables, and releasably secured to the lower end of the rod string for pushing. More details on wireline CPT probe deployment can be found in U.S. Pat. No. 6,644,423, the entire contents of which are incorporated herein by reference.

Notably, the push rod string 20 of the wireline system shown in FIG. 1 is equipped with a ring bit 22 at its lower end, and vehicle 10 includes means (discussed in more detail below) to selectively rotate ring bit 22 to 'drill' through tough soil layers.

Figure 2:
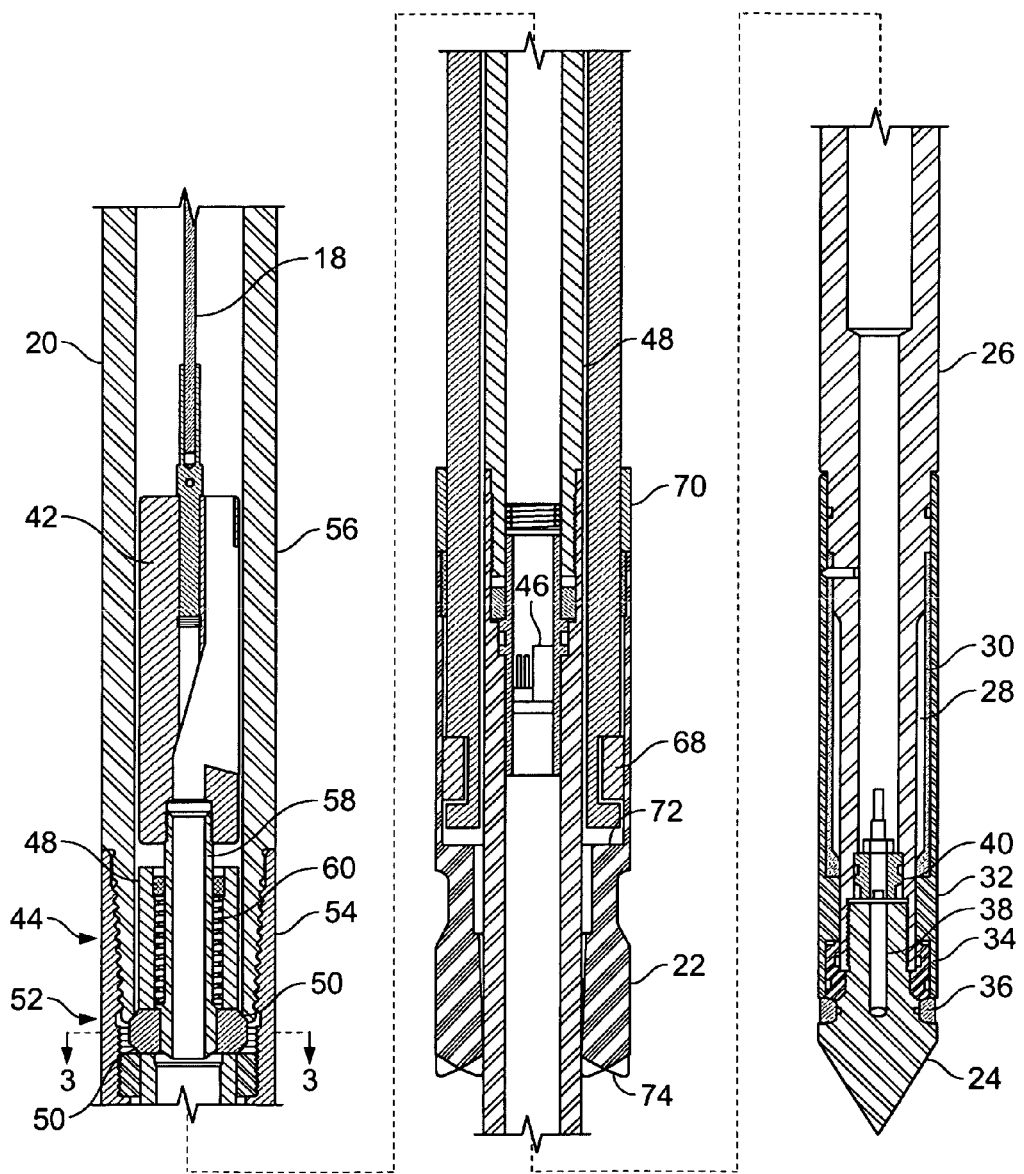
FIG. 2 is a cross-sectional view of a probe and casing end.

Referring next to FIG. 2, probe 12 includes a solid steel tip 24 threaded onto a steel mandrel 26. Strain gages secured to the outer surface 28 of the lower end of mandrel 26 are responsive to vertical (i.e., axial) load applied to tip 24. A second set of strain gages adhered to the inner surface of sleeve load cell 30 is responsive to axial friction load applied to the outer surface of friction sleeve 32 that bears against the lower end of load cell 30 but is otherwise axially unconstrained and is replaceable by unthreading tip 24 and removing a sealing retainer 34 at the lower end of the probe. A ring 36 of filter material just behind the tip covers inlets to a pressure sense passage 38 filled with a silicone gel and leading to a pressure sensor 40. The probe mandrel 26, latch assembly 44 and wireline connector 42 define inner passages for passing electrical wires (not shown) up through the probe and to the surface via the push rod string 20. A multi-pin electrical connector 46 sealed into the upper end of probe mandrel 26 allows for quick connection of the probe to the instrumentation cable (not shown).

Figure 3:
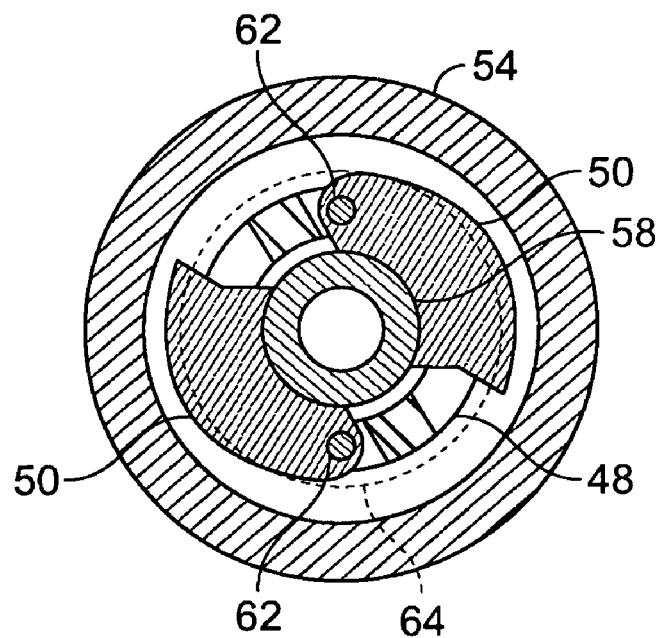
FIG. 3 is a lateral cross-sectional view taken at line 3—3 of FIG. 2, showing the probe-casing locking mechanism.
Figure 5:
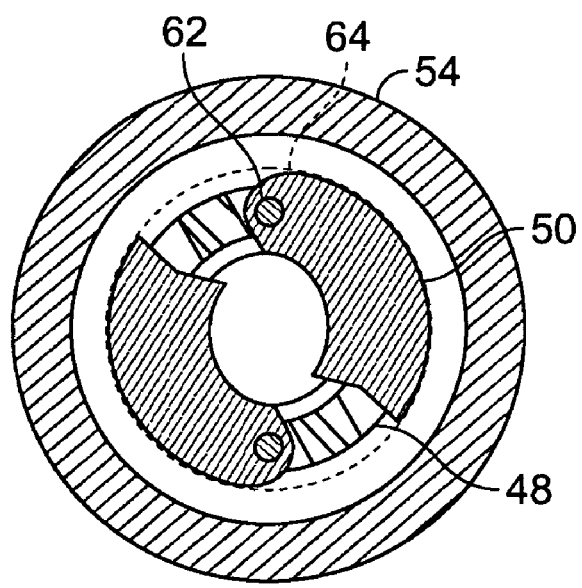
FIG. 5 is a lateral cross-sectional view taken at line 5—5 of FIG. 4.

Latch assembly mandrel 48 threadably attaches to the upper end of the probe mandrel 26 and carries two locking dogs 50 that are normally wedged outwardly to extend into an annular channel 52 between ring bit carrier 54 and lower rod section 56 to axially lock the probe with respect to the rod string. With the dogs 50 positioned as shown in FIGS. 2 and 3, significant axial push load can be applied to the probe by pushing on the upper end of the rod string. To release the probe from the rod string to enable wireline retrieval, tension is applied to wireline cable 18, pulling upward on latch plug 58 to compress coil compression spring 60 retained between an upper surface of plug 58 and a lower surface of a retaining ring held in the upper bore of mandrel 48. When plug 58 has been sufficiently raised with respect to mandrel 48, dogs 48 are free to rotate inwardly on pins 62 (see FIG. 3) to lie fully within the diameter of the inner bore 64 of the push rod string, as shown in FIGS. 4 and 5. Locking dogs 50 are rotated inwardly on pins 62 when tapered upper edge surfaces 66 of the locking dogs are forced against the lower end of lower rod section 56 as the probe is pulled upward with respect to the rod string by the wireline cable.

Still referring to FIG. 2, ring bit 22 is freely rotatable about the lower end of the rod string 20, and is kept from falling from the end of the rod string by a split ring 68 disposed in an outer groove in the lower end of the rod string and a bit stop sleeve 70 releasably threaded to the upper end of the ring bit. Downward push loads are transferred from the rod string directly into the ring bit at inner ring bit shoulder 72. Teeth 74 at the lower end of the ring bit dislodge soil and rock as the ring bit is rotated as discussed below. Teeth 74 may be in the form of replaceable inserts of particularly hard materials, such as carbide or diamond, as known in the drilling arts.

Referring next to FIG. 6, when ring bit 22 is to be rotated, such as to drill through a tough soil layer during a sounding, the instrumented probe is withdrawn from the rod string, and with the rod string remaining submerged in the soil, an inner drill rod string 76 is lowered through the outer rod string 20 until a tapered outer surface 78 of the lower end of a bit collet 80 at the end of the drill rod string seats against a tapered inner surface 82 of the ring bit, with a center bit 84 held securely in collet 80 and extending through the open end of the ring bit. Together, the lower surfaces of ring bit 22 and center bit 84 form a complete bit surface for abrading and dislodging soil, rock and other materials below the end of the outer rod string. Axial load can be applied through the outer rod string 20, or to both the outer rod string and inner drill rod string 76, as the drill rod string is rotated. Rotation of collet 80 and center bit 84 by drill rod string 76 also rotates ring bit 22, through torque applied at engaged tapered surfaces 78 and 82. During drilling, air or liquid (e.g., water) can be pumped down to the center bit along inner drill rod bore 86, forcing tailings up the annular space 88 between the inner and outer rod strings, such as through holes (not shown) through the side walls of the ring bit.

Figure 7:
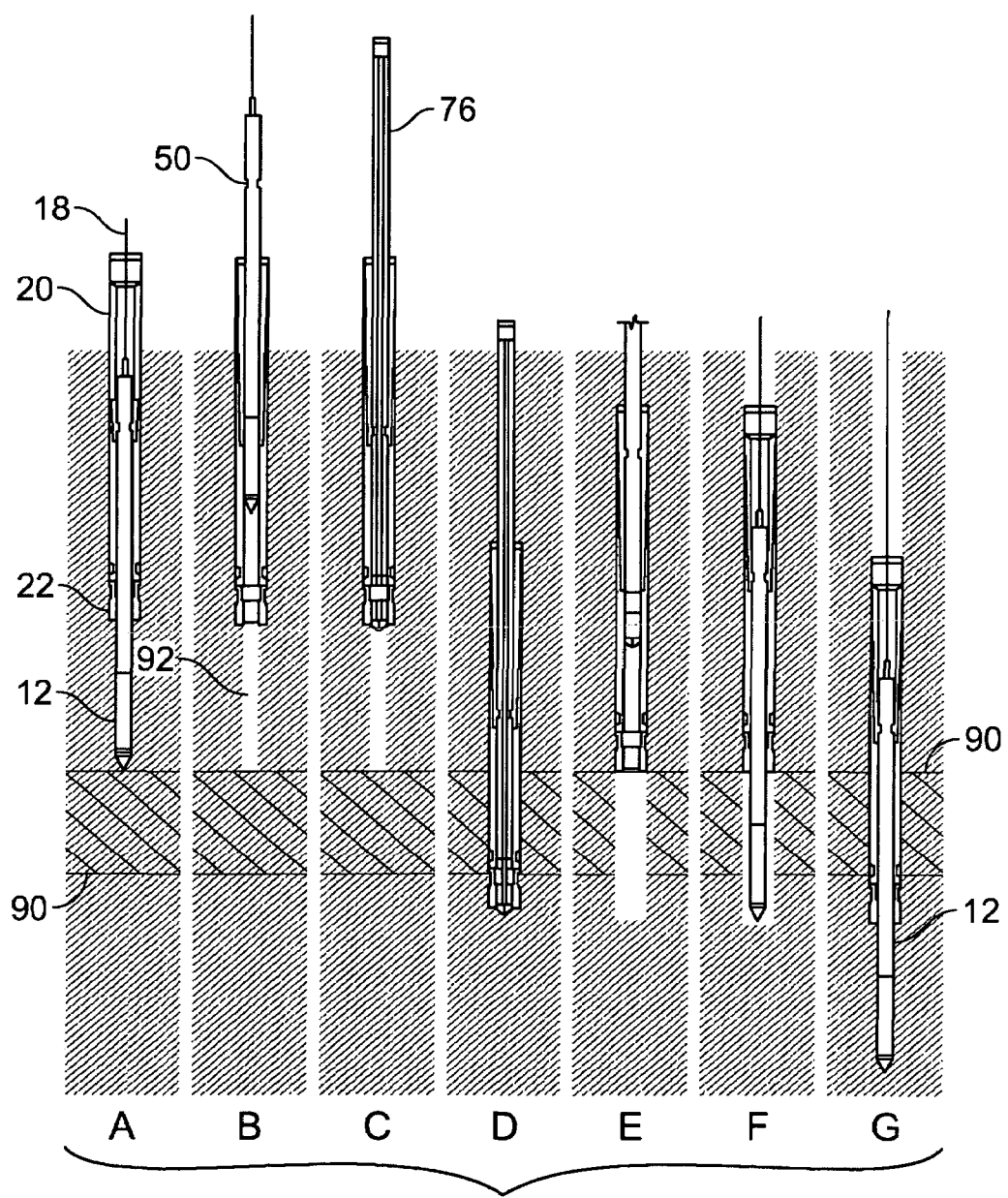
FIG. 7 sequentially illustrates a push-drill-push sequence for reaching a desired depth.

An operational sequence for breaching a very hard soil layer 90 is shown in FIG. 7. The wireline probe 12 and push rod string 20 are advanced together, but vertical push load applied only to the push rod string, until engagement of hard soil layer 90 causes the push load to reach a maximum safe load limit (frame A). The wireline probe is then withdrawn through the rod string (frame B) by pulling upward on the wireline cable 18, leaving a short exposed bore 92 in the soil below the remaining rod string. The inner drill rod string 76 is then lowered through the outer rod string until the center bit engages the ring bit (frame C). The outer rod string is then advanced while the center and ring bits are rotated by torque supplied through the drill rod string, with sufficient vertical load maintained on the drill rod string to maintain engagement of the matching tapered surfaces of the center and ring bits, to drill through the hard soil layer 90. When drilling loads indicate that the hard soil layer has been successfully passed (frame D), the inner drill rod and center bit are withdrawn to the surface (frame E), the outer rod string and ring bit being withdrawn only far enough to allow the probe 12 to be redeployed and locked into place extending through the lower end of the rod string (frame F), the tip of the probe placed to begin penetration into virgin soil at the bottom of the borehole as pushing resumes. Instrumented pushing can then begin again, the probe advancing and collecting data relating to conditions below the hard soil layer (frame G). This process can be repeated multiple times within a given sounding, as difficult soil layers are encountered, to obtain data at greater depths for a given push load. Upper sections of the outer rod string are omitted from this figure.

Figure 8:
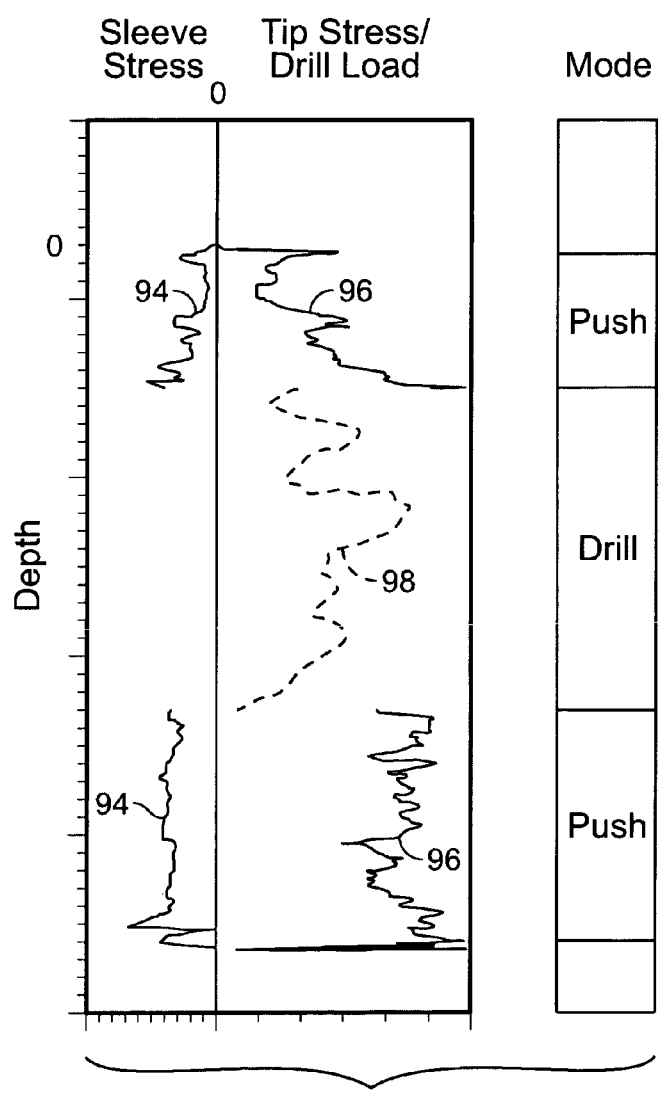
FIG. 8 is a representative log of a material property as a function of depth, obtained by the method illustrated in FIGS. 7.

FIG. 8 illustrates representative geotechnical data that could be obtained during the representative push sequence shown in FIG. 7. A soil classification algorithm estimates soil type as the probe progresses through the soil, and various sensors may be included in the probe to sense various other properties, such as pore pressure, fluorescence, resistivity, chemical composition, etc. As shown in FIG. 8, as the probe advances through the upper layer of soil, sleeve stress data 94 is gathered at very close depth or time intervals and logged as a function of depth, as is tip stress data 96. When the maximum required push load is exceeded, drill mode commences. During drilling, overall drill load 98, such as drill motor torque, may be measured and logged as a function of depth. When the drill load 98 has fallen below a certain minimum value, or the operator is otherwise convinced that the hard soil layer has been passed, the instrumented probe is redeployed and geotechnical data gathering resumes in a normal push mode. Drill load data 98 (such as torque, downward force or speed) or tailing composition may also be monitored during drilling to roughly determine soil stratification and composition for the depth range traversed during drilling. For example, torque, blows per minute (BPM) and downward load can all be maintained constant, with downward penetration monitored as data 98. Relative soil permeability can also be logged during air rotary drilling by monitoring the inflow and outflow of air, such as during a pause in drilling.

Figure 9:
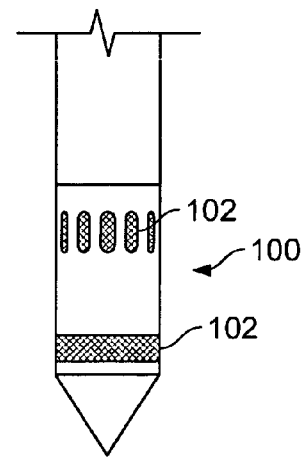
FIG. 9 is a cross-sectional view of a liquid or gas sampling probe.

Various material samplers and sensors can be incorporated into the instrumented probe, or deployed downhole in place of the probe during pauses between probe advances. For example, FIG. 9 illustrates a liquid or gas sampler 100 with sampling ports 102 in its outer surface, through which either liquid or gas from the surrounding soil may be drawn under vacuum or collected under pore pressure. The sampled material may be retained in a chamber within the sampler for retrieval at the surface when the sampler is withdrawn, or brought to the surface through a hose extending in parallel with the wireline cable on which the sampler is lowered. Although shown as a separate sampling module, similar sampling components may be incorporated into an instrumented probe, to enable sampling during geotechnical data collection. Soil sampling can be accomplished with a soil sampling module, such as the one described in U.S. Pat. No. 5,921,328, the contents of which are hereby incorporated by reference.

FIG. 10 illustrates a resistivity module 104 assembled to an instrumented geotechnical probe 12, for simultaneously gathering soil resistivity data and load data. Module 104 includes four electrically conductive contact rings 106 spaced apart from each other and the module housing 108 by insulators 110. The outer surfaces of rings 106, insulators 110 and module housing 108 are all of the same outer diameter to ensure good soil contact at each ring. The use of resistivity modules of this type is generally known in the art. In this context, such a combined probe and module assembly would be lowered through the outer rod string on a wireline cable below a latch assembly and wireline connector as in FIG. 2.

Those skilled in this art will understand from this disclosure how to incorporate various other sensors into various probes to be pushed to greater depths using the combined push and drilling techniques described herein. For example, subsurface material fluorescence can be logged for component analysis, such as by illuminating the material in situ by light of a chosen wavelength emitted through a window in the side of the probe, such as is taught in U.S. Pat. No. 5,902,939, the contents of which are hereby incorporated by reference.

Referring next to FIG. 11, a push system for deploying and retrieving the components discussed above includes a pair of primary push cylinders 112 securely mounted to the frame 114 of the push vehicle. A rigid push plate 116 spans the two push cylinder rods and is also rigidly attached to two threaded rods 118 that extend down to a primary rod clamp 120 positioned between the cylinders. Rollers or bushings 121 keep the primary rod clamp constrained to move in a vertical direction as the push cylinders 112 are extended and retracted. Clamp 120 includes a hydraulic clamp cylinder 122 coupled to one of a pair of opposing, curved clamp shoes between which the rod string 20 can extend. With the clamp cylinder 122 energized, the clamp applies high normal load to the outer surface of the rod string to rigidly clamp the rod for transmission of vertical load. With the clamp engaged, steady retraction of push cylinders 112 pushes clamp 120 and the clamped rod string downward at a relatively constant rate. Below the push system, rigidly secured to frame 114, is an auxiliary clamp 124 through which the rod string is deployed and retrieved. Auxiliary clamp 124 is hydraulically activated (by yet another hydraulic cylinder) to clamp against the outer surface of the rod string, and is particularly useful in holding up a partial rod string during rod string retrieval while the primary clamp is open. The arrangement of push cylinders 112, primary clamp 120 and auxiliary clamp 124 is generally known in the art.

Notably, however, this push system includes a drill head 126 with an electric or hydraulic drill motor 128 for engaging and rotating the inner rod string 76 during drilling mode. Drill head 126 is mounted to a frame 128 that is secured to the push system but can be rotated out of the way when not in use. The left side of frame 128, as viewed in FIG. 11, is a vertical hollow cylinder constrained between two large threaded nuts 130 on the left threaded rod 118, with a small amount of vertical clearance. The right side of frame 128 includes a vertical cylindrical section with a vertical slot (not shown) wide enough to clear the right threaded rod 118 when collar 132 is raised out of the cylindrical section as shown, to rotate the entire drill motor frame about the left threaded rod 118. Collar 132 is of greater outer diameter than the width of the slot in the drill motor frame, such that when collar 132 is lowered into place, it prevents rotation of frame 128. Thus, with the exception of collar 132 shown in a raised position, the push system of FIG. 11 is shown as it would be configured for drilling.

During drilling, an upper air swivel 134 engages and rotates the upper end of inner rod string 76 and provides a means of supplying pressurized air or liquid to the inner bore of the rod string. A lower air swivel 136 is clamped to the upper end of the outer rod string 20, sealing the annular space between the rod strings and providing a means of removing tailings and/or cutting fluids supplied to the downhole drilling components from the upper air swivel. The air swivels and drill head are not employed during direct pushing. During drilling, vertical load is provided by the push cylinders 112, while rotary torque is provided by drill head 126.

For situations where greater near-surface casing (i.e., outer rod string) support is required, auxiliary clamp 124 can accommodate tubes of up to about 120 millimeters in diameter. The push system can be employed to push a large diameter casing support tube, such as a tube with a 3.5 inch (89 mm) inner diameter and 4.0 inch (102 mm) outer diameter with a displaceable, pointed plug temporarily covering the lower end. Such a casing support tube can be embedded two to three meters into the soil. When the rod string and probe are later pushed through the support tube, the plug at the lower end of the tube is readily pushed aside by the probe.

Figure 12:
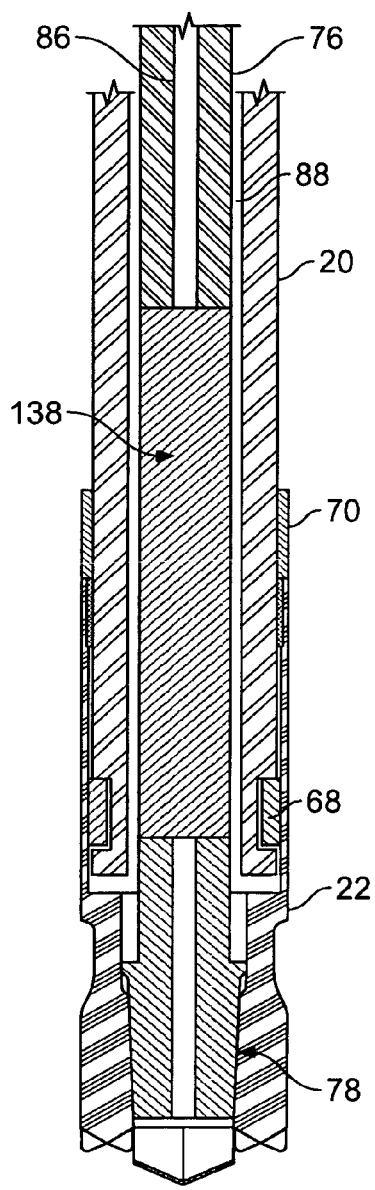
FIG. 12 is a cross-sectional view of the casing end with a pneumatic percussion hammer deployed.
Figure 13:
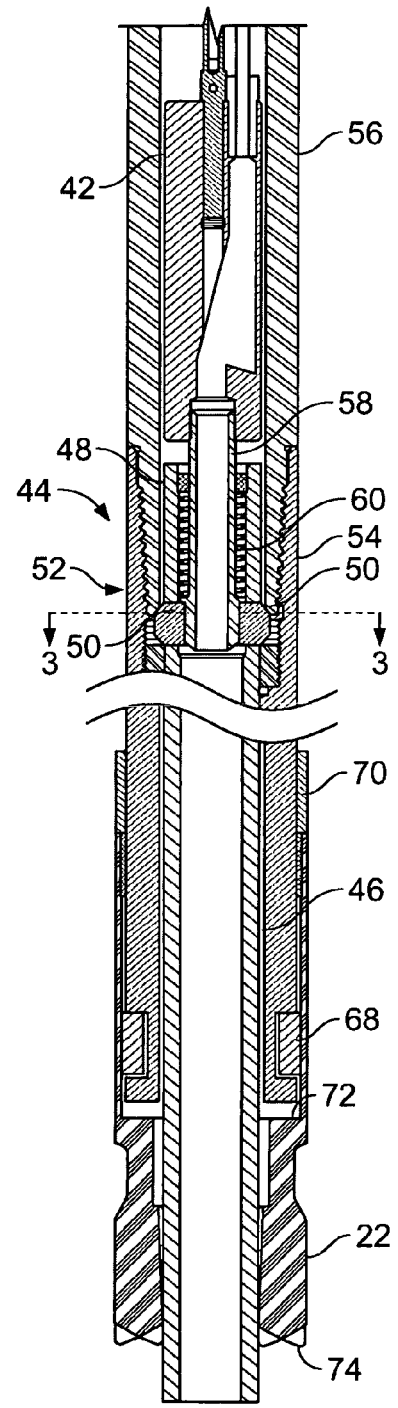
FIG. 13 is a cross-sectional view of the casing end with a wireline grouting module deployed.

Referring next to FIG. 12, in some cases a flow of high pressure air provided down the bore 86 of drill rod string 76 drives a downhole pneumatic hammer 138, to deliver a series of vertical impact loads to the center and ring bits during rotation. Exhaust air from hammer 138, along with tailings, flows back to the surface along inter-rod annulus 88. Suitable pneumatic hammers of an appropriate size are available commercially from Halco America of Benton, Ill., such as the Halco Dominator 100. When using such a hammer, we use a larger diameter rod string, with a 2.875 inch (73 mm) outer diameter and 2.375 inch (60 mm) inner diameter. When not using the hammer, we tend to employ a 2.0 inch by 1.25 inch (50 by 32 mm) rod string, with a 1.125 inch (29 mm) diameter probe.

The combination of direct push logging and drilling described above can be employed to advantage for several purposes. For example, such methods can be used to set up time domain reflectometry (TDR) slope stability sensors, such as by logging soil moisture or resistivity down to bedrock, withdrawing the moisture or resistivity probe through the rod string, deploying the center bit to drill about three meters into the bedrock, withdrawing the center bit and deploying a cable anchor below a grout module that, as retracted with the rod string, grouts the cable anchor into the bedrock with grout pumped down a hose through the rod string. The rod string is then fully withdrawn, leaving a coaxial cable extending from the embedded cable anchor to the ground surface. Such a sequence can also be employed to imbed a groundwater pump and filter into permeable rock, or to obtain water samples several meters into bedrock, or to install soil vapor monitoring points with sampling tubes extending to the surface. The method of anchoring cables described above is also useful for installing vertical electrode arrays (VEA's), instrumentation arrays for geophysical parameter monitoring, antennae for in-ground signal monitoring, and even anchor stays for supporting loads. The method described above enables in-situ logging of various subsurface parameters and installation of cables, wells or monitoring points on a single trip downhole, minimizing the risk of cross-contamination between strata by hydraulic communication along an open borehole, particularly when the grouting method described above is employed to grout the entire borehole as the rod string is withdrawn.

Drilling and direct push segments can be combined in various arrangements, as needed, to advance a given bore. While FIG. 8 illustrates data from a representative push-drill-push sequence, drill-push and push-drill (e.g., push-anchor) sequences are also envisioned.

A number of embodiments of the invention have been described. Nevertheless, it will be understood that various modifications may be made without departing from the spirit and scope of the invention. Accordingly, other embodiments are within the scope of the following claims.

What is claimed is:

1. A method of obtaining subsurface material property measurements in situ, the method comprising
    pushing a first measurement probe through soil at a controlled rate to a first depth while gathering material property data from sensors attached to the probe, the probe extending beyond a distal end of a casing pushed through the soil with the probe, the probe having an outer surface that slides linearly against the soil as the probe and casing are pushed through the soil;
    while leaving the casing in the soil, withdrawing the first probe from the distal end of the casing; and then
    rotating the distal end of the casing to displace subsurface materials to advance the casing with the first probe withdrawn.

2. The method of claim 1 further comprising, after advancing the casing, lowering a second measurement probe to extend through the distal end of the casing; and then
    pushing the second measurement probe through the soil at a controlled rate to a second depth while gathering additional material property data from sensors attached to the second probe.

3. The method of claim 2 wherein the second probe is the first probe, redeployed through the distal end of the casing.

4. The method of claim 2 wherein the second probe is lowered to the distal end of the casing on a wire line, and wherein force to push the second probe through the soil is applied through the casing.

5. The method of claim 2 wherein the casing is advanced by pushing as the second probe is pushed through the soil.

6. The method of claim 2 wherein the second probe includes a sensor responsive to load bearing against a distal end of the second probe in a push direction.

7. The method of claim 2 wherein the second probe includes a sensor responsive to soil friction load against an exposed surface of the second probe as the second probe is pushed through the soil.

8. The method of claim 2 wherein the second probe includes a sensor responsive to resistivity, soil moisture, fluorescence, pore water pressure or light.

9. The method of claim 2 wherein the second probe is configured to collect a sample of subsurface material.

10. The method of claim 2 further comprising combining data gathered with the first probe with data gathered from the second probe to create a subsurface property data log extending to the second depth.

11. The method of claim 10 wherein the data log includes a data-less region corresponding to soil through which the casing was advanced by rotating.

12. The method of claim 10 wherein the data log includes data obtained while rotating the distal end of the casing with the first probe withdrawn.

13. The method of claim 2 further comprising, after advancing the casing by rotating, pulling back on the casing to form clearance beyond the distal end of the casing to accommodate the second probe during lowering.

14. The method of claim 1 wherein withdrawing the first probe removes the first probe from the casing.

15. The method of claim 1 wherein withdrawing the first probe exposes an opening through the distal end of the casing, the method further including, prior to rotating the distal end of the casing, lowering a center bit into the opening, wherein rotating the distal end of the casing includes rotating the center bit.

16. The method of claim 15 wherein the center bit is lowered on a drive rod extending up along the casing, the center bit being rotated by rotating the drive rod.

17. The method of claim 15 wherein the distal end of the casing comprises a rotatable ring bit, and wherein the lowered center bit engages the ring bit, such that rotating the center bit rotates the ring bit.

18. The method of claim 1 wherein the casing is advanced, after the first probe is withdrawn, by air rotary or rotary wash drilling.

19. The method of claim 1 wherein the first probe includes a sensor responsive to load bearing against a distal end of the probe in a push direction.

20. The method of claim 1 wherein the first probe includes a sensor responsive to soil friction load against an exposed surface of the probe as the probe is pushed through the soil.

21. The method of claim 1 wherein the first probe includes a sensor responsive to resistivity, soil moisture, fluorescence, pore water pressure or light.

22. The method of claim 1 wherein the first probe is configured to collect a sample of subsurface material.

23. The method of claim 1 wherein the first probe is withdrawn from the distal end of the casing on a wire line, and wherein force to push the first probe through the soil is applied through the casing.

24. The method of claim 1 further comprising, after withdrawing the first probe, lowering a sampling module to the distal end of the casing and collecting a sample of subsurface material with the sampling module.

25. The method of claim 24 wherein the subsurface material comprises soil.

26. The method of claim 24 wherein the subsurface material comprises liquid.

27. The method of claim 24 wherein the subsurface material comprises gas.

28. The method of claim 24 wherein the sample is collected by advancing the casing after lowering the sampling module.

29. The method of claim 1 wherein the first probe extends at least three times an outer diameter of the first probe beyond the distal end of the casing, for obtaining material property measurements in soil undisturbed by advance of the casing.

30. The method of claim 1 wherein the first probe and the casing are pushed through the soil in a non-rotary sense.

31. The method of claim 1 wherein the first probe and the casing are pushed through the soil at a constant rate of about two centimeters per second.

32. The method of claim 1 including predetermining a push load at which the pushing of the first probe through the soil will be terminated and the first probe withdrawn.

33. The method of claim 1 further comprising:
prior to rotating the distal end of the casing, lowering a percussion hammer to engage the distal end of the casing, and,
while rotating the distal end of the casing, activating the percussion hammer to advance the casing through the soil.

34. The method of claim 33 wherein the percussion hammer is activated pneumatically.

35. The method of claim 1 further comprising withdrawing the casing from the soil while filling an exposed hole beneath the withdrawn casing with grout supplied through the casing.

36. The method of claim 35 wherein the grout is delivered through a tube extending from above ground to a grout outlet module lowered into the casing after the first probe is withdrawn.

37. The method of claim 1 wherein rotating the distal end of the casing advances the casing into bedrock.

38. The method of claim 37 further comprising setting an anchor into the bedrock.

39. The method of claim 1 further comprising lowering a casing support tube into the soil, the support tube extending above the soil and defining an annular passage through which the casing is advanced.

40. The method of claim 39 wherein the support tube extends into the soil to a depth of at least two meters.

41. The method of claim 1 wherein the distal end of the casing comprises a rotatable ring bit, and wherein a major extent of the casing is pushed in a non-rotary sense as the ring bit is rotated.

42. The method of claim 1 further comprising, while rotating the distal end of the casing, monitoring drilling parameters to determine relative soil properties.

43. A method of obtaining subsurface material property measurements in situ, the method comprising
rotating a distal end of a hollow casing to displace subsurface materials to advance the casing through soil;
lowering a measurement probe through the advanced casing;
extending the lowered measurement probe through the distal end of the casing to engage soil below the casing;
advancing the extended probe through the soil at a controlled rate to a first depth while gathering material property data from sensors attached to the probe, the probe having an outer surface that slides linearly against the soil as the probe and casing are advanced through the soil.

44. The method of claim 43 wherein the distal end of the casing is rotated by torque applied by a drive rod extending down through the casing to engage the distal end of the casing.

45. The method of claim 44 wherein the drive rod includes a center bit that rotates with the distal end of the casing to displace subsurface materials.

46. The method of claim 44 further including, prior to lowering the measurement probe, removing the drive rod from the casing.

47. The method of claim 46 wherein the distal end of the casing comprises a ring bit rotated with respect to the casing by the drive rod.

48. The method of claim 43 wherein the casing is advanced by air rotary or rotary wash drilling.

49. The method of claim 43 wherein the probe is lowered into the casing on a wire line, and wherein force to push the probe through the soil is applied through the casing.

50. The method of claim 43 wherein the probe includes a sensor responsive to load bearing against a distal end of the probe in a push direction.

51. The method of claim 43 wherein the probe includes a sensor responsive to soil friction load against an exposed surface of the probe as the probe is pushed through the soil.

52. The method of claim 43 wherein the probe includes a sensor responsive to resistivity, soil moisture, fluorescence, pore water pressure or light.

53. The method of claim 43 wherein the probe is configured to collect a sample of subsurface material.

54. The method of claim 43 wherein the probe extends at least-three times an outer diameter of the probe beyond the distal end of the casing, for obtaining material property measurements in soil undisturbed by advance of the casing.

55. The method of claim 43 wherein the probe and casing are advanced together by pushing through the soil in a non-rotary sense.

56. The method of claim 43 wherein rotating the distal end of the casing includes activating a percussion hammer engaging the distal end of the casing, to advance the casing through the soil.

57. The method of claim 56 further comprising, prior to lowering the measurement probe, withdrawing the percussion hammer from the casing on a wireline.

58. The method of claim 43 further comprising, while rotating the distal end of the casing, monitoring drilling parameters to determine relative soil properties.

* * * * *